(12) United States Patent
Nestler et al.

(10) Patent No.: US 6,727,383 B1
(45) Date of Patent: Apr. 27, 2004

(54) METHOD FOR PRODUCING ACRYLIC ACID AND ACRYLIC ACID ESTERS

(75) Inventors: Gerhard Nestler, Ludwigshafen (DE); Jürgen Schröder, Ludwigshafen (DE); Otto Machhammer, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/647,561

(22) PCT Filed: Mar. 24, 1999

(86) PCT No.: PCT/EP99/01995

§ 371 (c)(1), (2), (4) Date: Oct. 2, 2000

(87) PCT Pub. No.: WO99/50219

PCT Pub. Date: Oct. 7, 1999

(30) Foreign Application Priority Data

Mar. 31, 1998 (DE) .......................... 198 14 387

(51) Int. Cl.⁷ .............................................. C07C 51/42
(52) U.S. Cl. ................. 562/600; 560/205; 562/598
(58) Field of Search ................ 562/598, 600, 562/512

(56) References Cited

U.S. PATENT DOCUMENTS 3,844,903 A   10/1974 Willersinn et al.
5,154,800 A   10/1992 Berg
5,817,865 A * 10/1998 Machhammer et al. ...... 560/208

FOREIGN PATENT DOCUMENTS

| DE | 1 618 141 | 10/1970 |
| DE | 2 121 123 | 11/1972 |
| DE | 2 136 396 | 2/1973 |
| DE | 34 29 391 | 2/1986 |
| DE | 43 08 087 | 9/1994 |
| EP | 0 009 545 A1 * | 4/1980 |

* cited by examiner

Primary Examiner—Johann Richter
Assistant Examiner—Karl J Puttlitz
(74) Attorney, Agent, or Firm—Oblon, Spivak, McClelland, Maier & Neustadt, P.C.

(57) ABSTRACT

A process for preparing acrylic acid and/or acrylates which comprises the following stage A and, if desired, B and C:

A: cooling a gaseous reaction mixture which comprises acrylic acid and is obtained in the gas-phase oxidation to prepare acrylic acid, using oligomeric acrylic acid or a mixture of acrylic acid and oligomeric acrylic acid, to give a gaseous mixture comprising acrylic acid and a quench bottom product which comprises oligomeric acrylic acid;

B: separating the gaseous mixture comprising acrylic acid, to give a low-boiling fraction, a crude acrylic acid, and a bottom product, which comprises oligomeric acrylic acid;

C: esterifying the crude acrylic acid obtained in stage B by means of one or more alkanols.

13 Claims, 1 Drawing Sheet

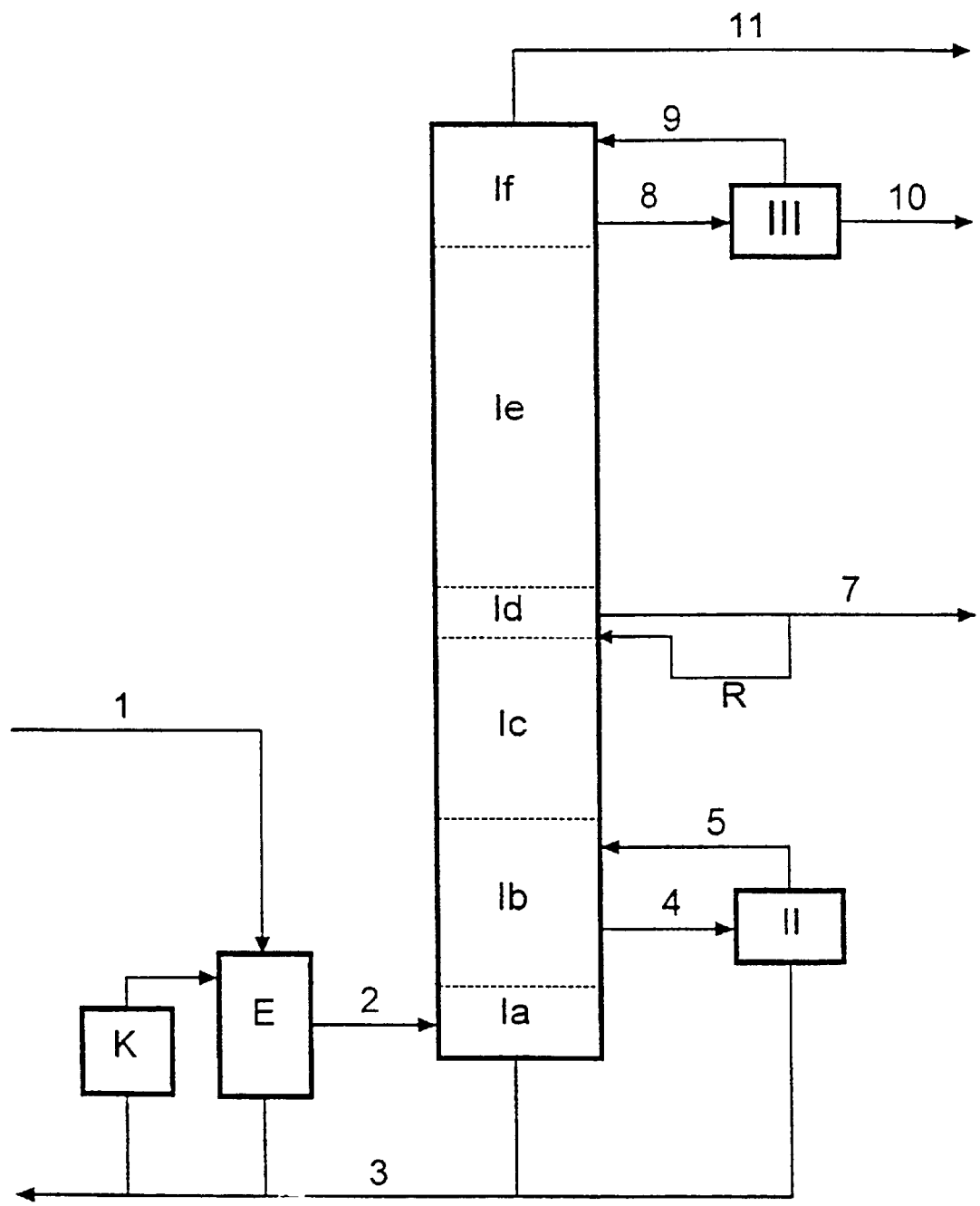

METHOD FOR PRODUCING ACRYLIC ACID AND ACRYLIC ACID ESTERS

BACKGROUND OF THE INVENTION

1. Field of the Invention

The present invention relates to a process for preparing acrylic acid that involves using oligomeric acrylic acid or a mixture comprising acrylic acid and oligomeric acrylic acid to cool a gaseous reaction mixture which comprises acrylic acid and is obtained in the gas-phase oxidation to prepare acrylic acid, and that produces a gaseous mixture comprising acrylic acid. It also relates to a process for the preparation of acrylates. Moreover, it relates very generally to the use of oligomeric acrylic acid or of a mixture comprising acrylic acid and oligomeric acrylic acid to cool a gaseous reaction mixture obtained in the gas-phase oxidation to prepare acrylic acid.

2. Description of the Background

Because of its highly reactive double bond and the acid function, acrylic acid is a valuable monomer for preparing addition polymers, for example, for aqueous polymer dispersions suitable as adhesives.

One route to acrylic acid is the gas-phase oxidation of propylene and/or acrolein with oxygen or gases comprising oxygen in the presence of catalysts at elevated temperature, preferably with dilution of the reactants with inert gases and/or steam owing to the high heat of reaction.

Catalysts employed in this oxidation are generally multicomponent oxide-type systems based, for example, on oxides of molybdenum, of chromium, of vanadium or of tellurium.

However, this process leads not to pure acrylic acid but rather to a gas mixture which in addition to acrylic acid comprises secondary components—mainly unreacted acrolein and/or propylene, steam, oxides of carbon, nitrogen, oxygen, acetic acid, formaldehyde, benzaldehyde, fufurals, and maleic anhydride—from which the acrylic acid must subsequently be separated.

Isolation of the acrylic acid from the gaseous reaction mixture is generally carried out by countercurrent absorption using, for example, a high-boiling solvent or solvent mixture and a plurality of subsequent distillative processing steps, as is described, for example, in DE-A 21 36 396 and DE-A 43 08 087. In EP-B 0 009 545, U.S. Pat. No. 5,154,800, DE-A 34 29 391 and DE-A 21 21 123 absorption takes place first with water/aqueous acrylic acid in countercurrent and is followed by extractive or azeotropic distillation.

Disadvantages associated with these processes are that in general they are technically complex and energy-intensive and that for the absorption and, where appropriate, extraction an additional organic solvent/solvent mixture is required which has to be separated off again in a separate distillation step and possibly purified before being used again.

A further disadvantage of these processes is that the acetic acid obtained alongside acrylic acid in the oxidation of propylene (purity of the acetic acid: from 0.5 to 10% by weight relative to the amount of acrylic acid) has to be separated off in a complex distillation stage. Because of the small differences in boiling point and the great tendency of acrylic acid to polymerize, this is a difficult task, as can be seen, inter alia, from U.S. Pat. No. 3,844,903.

In view of the known fact that acrylic compounds have a high tendency to undergo addition polymerization, processes operating with multistage distillative workup are disadvantageous in very general terms since they heighten the polymerization tendency of the acrylic acid.

SUMMARY OF THE INVENTION

It is now the object of the present invention to provide a simple process for obtaining acrylic acid which first requires no additional solvent/absorbent or extractant and second is energetically favorable in its implementation.

We have found that this object is achieved by the present invention, which provides a process for preparing acrylic acid comprising the following stage A:

A: cooling a gaseous reaction mixture which comprises acrylic acid and is obtained in the gas-phase oxidation to prepare acrylic acid, using oligomeric acrylic acid or a mixture of acrylic acid and oligomeric acrylic acid, to give a gaseous mixture comprising acrylic acid and a quench bottom product which comprises oligomeric acrylic acid.

DETAILED DESCRIPTION OF THE INVENTION

The term "gaseous reaction mixture which comprises acrylic acid" embraces, for the purposes of the invention, all reaction mixtures obtained in the gas-phase oxidation to prepare acrylic acid.

If propylene/acrolein are used as starting materials to prepare acrylic acid, the gaseous reaction mixture concerned is obtained with a temperature of approximately 200 to 300° C. from the gas-phase oxidation and comprises from about 1 to about 30% by weight of acrylic acid with the following byproducts: unreacted propylene (from about 0.05 to about 1% by weight), acrolein (from about 0.001 to about 2% by weight), propane (from about 0.01 to about 2% by weight), steam (from about 1 to about 30% by weight), oxides of carbon (from about 0.05 to about 15% by weight), nitrogen (from 0 to about 90% by weight), oxygen (from about 0.05 to about 10% by weight), acetic acid (from about 0.05 to about 2% by weight), propionic acid (from about 0.01 to about 2% by weight), aldehydes (from about 0.05 to about 3% by weight), and maleic anhydride (from about 0.01 to about 0.5% by weight).

This gaseous reaction mixture is cooled by means of oligomeric acrylic acid or a mixture comprising acrylic acid and oligomeric acrylic acid, generally to a temperature from approximately 100 to approximately 190° C., preferably from approximately 120 to approximately 180° C. and, in particular, from approximately 130 to approximately 160° C., to give a further gaseous mixture comprising acrylic acid.

As the cooling apparatus it is possible to employ any prior art apparatus known for this purpose, with preference being given to the use of Venturi scrubbers or spray coolers (quench), especially the latter.

The term "oligomeric acrylic acid" used in accordance with the invention here comprises the product formed by addition of the carboxyl group onto the olefinic double bond by Michael addition, having the following formula I:

$$CH_2=CHCO_2-(CH_2CH_2CO_2)_n-H \qquad n=1-10$$

Oligomeric acrylic acid is always formed during the preparation of acrylic acid and is influenced by the temperature and the residence time but cannot be influenced or prevented by inhibitors.

The resultant gaseous mixture comprising acrylic acid is preferably separated in a stage B to give a crude acrylic acid, a low-boiling fraction, and a bottom product which comprises oligomeric acrylic acid. In particular, the separation of stage B is carried out in a distillation column and this is done preferably such that the acrylic acid is obtained by way of a sidestream takeoff of a distillation column.

The procedure here is generally as follows:

The gaseous mixture from stage A, comprising acrylic acid, is passed into the lower part of a distillation column, in which the gaseous constituents and the low boilers, especially aldehydes, acetic acid and water, are separated off via the top of the column.

The acrylic acid is drawn off as crude acrylic acid in the lower third of the distillation column via a sidestream takeoff.

The high boilers, principally oligomeric acrylic acid, are obtained in the bottom (liquid phase) of the distillation column.

The columns which can be employed for the process of the invention are not subject to any particular restriction. In principle, suitable columns are all those having internals which provide for effective separation.

Suitable column internals are all customary internals, especially trays, and random and/or structured packings. Of the trays, preference is given to bubble-cap trays, sieve trays, valve trays and/or dual-flow trays. The column comprises at least one cooling apparatus. Suitable such apparatus comprises all those heat transfer devices or heat exchangers where the heat liberated during the condensation is dissipated indirectly (externally). All customary apparatuses can be employed for this purpose, with preference being given to tube bundle heat exchangers, plate heat exchangers, and air coolers. Suitable cooling media in the case of an air cooler are, appropriately, air, and in the case of other cooling apparatuses are liquid coolants, especially water. Where only one cooling apparatus is provided it is installed at the top of the column, where the low-boiling fraction is condensed out.

The skilled worker will readily be able to determine the number of cooling apparatuses required, as a function of the desired purity of the condensed fractions and thus of the components, the purity of the condensed components being determined essentially by the installed separation efficiency of the column, i.e., the column height, the number of trays, and the energy introduced by the gaseous mixture from stage A that is to be condensed. Judiciously, when two or more cooling apparatuses are present, they are installed in different sections of the column.

In the case, for example, of a gaseous mixture from stage A which comprises not only a high proportion of uncondensable components but also a high-boiling, middle-boiling and low-boiling fraction, one cooling apparatus may be provided in the lower section of the column to condense out the high-boiling fraction and one cooling apparatus may be provided at the top of the column to condense out the low-boiling fraction. The condensed fractions are led off by way of sidestream takeoffs at the respective sections in the column. Depending on the number of components in the high-boiling, middle-boiling and low-boiling fraction it is possible in each case to provide two or more sidestream takeoffs. The fractions drawn off by way of the sidestream takeoffs can then be subjected to further purification stages, examples being distillative or extractive separation procedures or a crystallization, depending on the desired purity of the components.

In one preferred embodiment of the invention there is one takeoff for high boilers, one takeoff for low boilers and one or two takeoffs for middle boilers.

The pressure within the column depends on the amount of uncondensable components and is preferably 0.5–5 bar absolute, especially 0.8–3 bar absolute.

The temperature in the region of the separating device in which the low boilers—that is, essentially and typically, aldehydes, acetic acid and water—are separated off is from approximately 25 to approximately 50° C., preferably from approximately to approximately 40° C.; the temperature in the region in which the crude acrylic acid is obtained is from approximately 70 to 110° C., preferably from approximately 80 to approximately 100° C.; and the bottom temperature is maintained at from approximately 90 to approximately 140° C., in particular from approximately 115 to 135° C.

The precise operating conditions for the column, such as temperature and pressure regime, arrangement and positioning of the cooling apparatus(es), positioning of the sidestream takeoffs for drawing off the desired fractions, choice of column height and column diameter, number and spacing of the separation-effective internals/trays in the column, and the nature of the separation-effective column internals, can be determined by the skilled worker in dependence on the particular separation task, within the scope of experiments that are customary in the art.

In the presence of a high-boiling fraction, a middle-boiling fraction, a low-boiling fraction and uncondensable component(s) in the gaseous mixture comprising acrylic acid (gaseous mixture), the process is advantageously conducted as shown in the Figure and as described below, the column being subdivisible into different sections in which different technical processing problems are solved.

The reference characters in the Figure in this case denote the individual sections in the column (I.a to I.f) and separate sections/apparatuses upstream of the column (E), incoming and outgoing lines (1–11), and the cooling circuits II and III.

E. Quench:

Cooling the gaseous mixture

In the installation E the gaseous mixture is introduced and cooled. This can be done, for example, by direct cooling with the cooling medium used being the high-boiling fraction comprising oligomeric acrylic acid that is condensed in the next section of the column. In this case the gaseous mixture from line 1 is cooled in a quench E and is supplied via line 2 to the bottom region I.a of the column. By way of line 3, the condensed high-boiling fraction is passed back into the quench for cooling of the gaseous mixture. Here, the oligomeric acrylic acid (high boiler) which is passed back for cooling, can be cooled in a cooler (K), for example to from 80 to 150° C. A fraction of the stream, usually from 0.1 to 10% by weight based on 100% by weight of acrylic acid, is removed from the process.

I.b Cooling Circuit II:

Condensing the high-boiling fraction

In the column section I.b, the heat of condensation is dissipated externally by means of a heat exchanger with, for example, water as the cooling medium, by taking off condensed high-boiling fraction from the column by way of line 4, cooling it and recycling one portion of the cooled, condensed high-boiling fraction to the column via line 5, while another portion, corresponding to the level in the quench, is passed back into the quench E by way of line 3. The recycled, condensed high-boiling fraction is guided in countercurrent to the ascending gaseous mixture.

I.c Cooling Circuit II→Sidestream Takeoff:

Concentrating high boilers

In the column section I.c between column section I.b (cooling circuit II) and I.d (sidestream takeoff), toward the cooling circuit II, the high-boiling fraction is concentrated by distillation and condensed out from the gaseous mixture is guided upward in countercurrent.

I.d Sidestream Takeoff:

Drawing off the middle-boiling fraction

By way of sidestream takeoff 7 in the column section I.d the desired target component, acrylic acid, is taken off in liquid form as crude acrylic acid by way, for example, of a catchplate and some of it is passed as a return flow (R) through a heat exchanger if desired, below the sidestream takeoff 7 and back into the column.

I.e Sidestream Takeoff→Cooling Circuit III:

Concentrating the middle boilers

In the column section I.e between column section I.d (sidestream takeoff 7) and I.f (cooling circuit III), the middle-boiling fraction of the gaseous mixture is concentrated by distillation from the gaseous mixture guided upward, the middle-boiling fraction being concentrated toward the sidestream takeoff (region I.d).

I.f Cooling Circuit III:

Condensing the low-boiling fraction

In the column section I.f of the external cooling circuit III, the low-boiling fraction is condensed from the gaseous mixture passed upward in countercurrent. As with the cooling circuit II, the heat of condensation is dissipated externally by way of cooling circuit III by means of a heat exchanger with, for example, water as the cooling medium by drawing off condensed low-boiling fraction by way of line 8, cooling it and recycling one portion of the cooled, condensed low-boiling fraction to the column via line 9 while the other portion is removed via line 10. The uncondensed gases are drawn off from the top of the column via line 11, it also being possible if appropriate to superheat the gas stream in order to prevent further condensation in the vapor pipe.

The gas is preferably passed back via line 11 as circulation gas into the acrylic acid preparation stage.

Further details regarding this procedure are given in DE-A 197 40 253, the content of which is included in its entirety in the context of the present application by reference.

During the separation procedure a polymerization inhibitor is added for stabilization, such as phenothiazine, a phenolic compound, an N—O compound, or a mixture of two or more of these compounds, preferably phenothiazine or hydroquinone, a mixture of phenothiazine and hydroquinone, hydroquinone monomethyl ether, p-nitrosophenol, nitrosodiethylaniline or tetramethylpiperidine-1-oxyls, as are described in DE-A-16 18 141.

The low boilers obtained after the separation are removed from the separating apparatus and then passed back in whole or in part, with or without the addition of a polymerization inhibitor, as a return flow into the upper part of the separation apparatus in order therein to facilitate the condensation of the low boilers contained in the gaseous mixture comprising acrylic acid.

The crude acrylic acid obtained as a middle boiler, preferably via a sidestream takeoff, is subjected to crystallization or distillation by a prior art technique to give a pure acrylic acid. In this case, mother liquor from the crystallization, in whole or in part, and/or, if appropriate, a portion of the crude acrylic acid, is supplied to the column below the sidestream takeoff.

Furthermore, the crude acrylic acid obtained in accordance with the invention can also be subjected to esterification by a prior art technique, as is described, for example, in DE-A-195 47 485 and in the prior art cited therein.

The present invention therefore additionally provides a process for preparing an acrylate, or a mixture of two or more thereof, which in addition to the above-defined stages A and B comprises a further stage C:

C: esterifying the crude acrylic acid obtained in stage B by means of one or more alkanols.

For further details regarding the esterification of acrylic acid reference is made to the abovementioned DE-A 195 47 485 and the prior art cited therein, the content of which is incorporated in its entirety by reference in the context of the present application.

The quench bottom product obtained in stage A consists predominantly—that is, to the extent of from 60 to 100% by weight—of oligomeric acrylic acid. This oligomeric acrylic acid can be used further, within the scope of the present process, as follows:

1. A portion—corresponding to the level in the quench—of the high-boiling fraction obtained in stage B is supplied to the quench by way of a cooling device, preferably a conventional heat exchanger, cooled to a temperature in the range of in general from approximately 40 to approximately 100° C., preferably from approximately 80 to approximately 100° C., and is passed back into stage A in order to cool the gaseous reaction mixture comprising acrylic acid and obtained in the gas-phase oxidation to prepare acrylic acid.

2. The oligomeric acrylic acid removed from the quench is cracked back thermally into acrylic acid, preferably in the presence of a catalyst such as are described, for example, in Ullmanns Encyklopadie der techn. Chemie, 4th Ed., vol. 7, p. 83, preferably a mineral acid or an organic acid other than acrylic acid, such as an alkyl- or arylsulfonic acid, especially sulfuric, phosphoric, methanesulfonic or p-toluenesulfonic acid. The products of cracking, i.e., primarily acrylic acid and diacrylic acid, which are obtained as a distillate in this process, can then be either combined with the crude acrylic acid obtained in stage B and worked up or processed further, or recycled to stage A in order to cool the gaseous reaction mixture obtained in the gas-phase oxidation. In the course of cooling the gaseous reaction mixture, this acrylic acid evaporates and so is recovered.

3. A further advantageous embodiment of the present invention consists in cracking the resultant oligomeric acrylic acid together with the oxy esters that are usually obtained during the preparation of acrylates, as is described in DE-A 195 47 485. Accordingly, the bottom product obtained in the esterification, which comprises the oxy esters, is first of all separated off and then oligomeric acrylic acid is added directly to this bottom product; the oxy esters present in the bottom product are then cracked in the presence of acid catalysts other than oligomeric acrylic acid, by the action of elevated temperature, or the oxy esters are first of all separated off by distillation from the bottom product from the preparation of acrylates, oligomeric acrylic acid is added to the distillate, and cracking takes place in the presence of acid catalysts other than oligomeric acrylic acid under the action of elevated temperature.

Here, the oligomeric acrylic acid has a proportion of the mixture to be cracked from about 10 to about 50% by weight, preferably from about 10 to about 40% by weight.

Preferably, in addition to the acidic esterification catalyst which may already be present, and which is other than oligomeric acrylic acid, further acids from the group consisting of mineral acids, such as sulfuric or phosphoric acid, and of organic acids other than oligomeric acrylic acid, such as alkyl- or arylsulfonic acids, especially methanesulfonic acid or p-toluenesulfonic acid, are added to the mixture that is to be cracked. The overall amount of acid other than oligomeric acrylic acid can in this case be from about 1 to about 20% by weight, preferably from about 5 to about 15% by weight, based on the amount of the product to be cracked. The mixture obtained in this cracking operation, which comprises primarily the acrylate, alkanol and acrylic acid, is passed either to esterification or to the workup of the crude acrylate.

Further details regarding this cracking of oligomeric acrylic acid and of the bottom product from the preparation of acrylates can be taken from the abovementioned DE-195 47 485, the content of which is incorporated in its entirety by reference in the context of the present application.

As emerges from the text above, accordingly, the present invention also provides a process for preparing acrylic acid, or an acrylate, in which a portion of the quench bottom product obtained in stage A or of the bottom product obtained in stage B, or a mixture thereof, each comprising oligomeric acrylic acid, are heated in the presence of a catalyst, to give a mixture which comprises acrylic acid, and provides a process for preparing acrylic acid, or an acrylate, in which a portion of the quench bottom product obtained in stage A, which comprises oligomeric acrylic acid, and high-boiling byproducts obtained in the esterification of stage C, are heated in whole or in part in the presence of a catalyst, to give a mixture which comprises acrylic acid and acrylate.

The mixture comprising acrylic acid can be used in whole or in part for cooling in stage A. Furthermore, the mixture comprising acrylic acid and the mixture comprising acrylic acid and acrylate can be passed back, in whole or in part, individually or in combination, into the esterification stage.

The process of the invention can be carried out continuously or batchwise, with the continuous implementation being preferred.

The process of the invention has the following advantages:
1. No extraneous absorbent or extractant is required. The oligomeric acrylic acids which are always obtained in the preparation of acrylic acid are employed per se to cool the gaseous reaction mixture comprising acrylic acid and obtained in the gas-phase oxidation to prepare acrylic acid.
2. In technical terms the process is comparatively simple, since only one separating device is required. Since the reaction mixture obtained in the gas-phase oxidation is merely cooled and converted to another gaseous mixture, the implementation of the process is also relatively favorable from an energetic standpoint.
3. The oligomeric acrylic acid can be reconverted into target product, i.e., acrylic acid.

The crude acrylic acid obtained in accordance with the invention can be processed directly to pure acrylic acid by crystallization or distillation, or can be esterified with alkanols.

In its most general form, the present invention also provides for the use of oligomeric acrylic acid or of a mixture of acrylic acid and oligomeric acrylic acid to cool a gaseous reaction mixture comprising acrylic acid and obtained in the gas-phase oxidation to prepare acrylic acid.

The present invention will now be elucidated with reference to an example.

EXAMPLE

Two-stage catalytic oxidation of propylene with molecular oxygen gave, in conventional manner, a gaseous reaction mixture having the following composition:
  9.84% by weight acrylic acid,
  0.4% by weight acetic acid,
  4.42% by weight water,
  0.11% by weight acrolein,
  0.21% by weight formaldehyde,
  0.07% by weight maleic anhydride, and also propionic acid, furfural, propane, propene, nitrogen, oxygen, and carbon oxides.

This gaseous reaction mixture was cooled to 140° C. in a spray cooler (quench) by introducing a spray of oligomeric acrylic acid (800 l/h). During this procedure, the oligomeric acrylic acid was circulated via a heat exchanger, and a temperature of 95° C. was established.

Superfluous oligomeric acrylic acid was removed at a rate of 3 g/h in a level-controlled procedure.

The cooled, gaseous mixture comprising acrylic acid was passed via a droplet separator (cyclone) into the lower part of a distillation column which was equipped with 60 dual-flow trays, a sidestream takeoff between trays 14 and 15, and a spray condenser at the top of the column. The temperature at the top of the distillation column was 34° C., the bottom temperature of the distillation column 100° C.

The distillate obtained in the spray condenser, which consisted primarily of water and acetic acid, underwent removal of 20% of itself, had 2000 ppm of hydroquinone added, and then was applied again as reflux to the topmost column tray. Via the sidestream takeoff, 350 g/h of crude acrylic acid was removed in liquid form from the distillation column. This crude acrylic acid contained 97.3% by weight acrylic acid, 0.9% by weight of acetic acid, 0.05% by weight propionic acid, 0.01% by weight acrolein, 0.03% by weight furfural, and 1.5% by weight water.

A portion—corresponding to the level in the quench—of the high-boiling fraction obtained in the bottom of the distillation column was supplied to said quench. The other portion of the high-boiling fraction was passed through a heat exchanger and run onto the fifth column tray, where a temperature of 100° C. was established.

The bottom product removed from the quench bottom, comprising a proportion of oligomeric acrylic acid of about 80% by weight, was heated at 150° C. for 3 hours in the presence of 1% by weight of sulfuric acid in a heatable 21 stirred reactor, and the cracking products which were formed were drawn off continuously in gaseous form via a splash-guard and condensed. The distillate (91% by weight of the amount fed in) consisted primarily of acrylic acid and diacrylic acid, and was stabilized with 500 ppm of phenothiazine and passed likewise to the cooling circuit in order to cool the gaseous reaction mixture.

We claim:
1. A process for preparing acrylic acid comprising the following stage A:
   A: cooling a gaseous reaction mixture (1) which comprises acrylic acid with oligomeric acrylic acid or a mixture comprising acrylic acid and oligomeric acrylic acid, to give a gaseous mixture (2) comprising acrylic acid and a quench bottom product which comprises oligomeric acrylic acid, wherein the gaseous reaction mixture (1) is obtained by gas-phase oxidation.

2. The process as claimed in claim 1, wherein the gaseous reaction mixture comprising acrylic acid is cooled in stage A to a temperature from 120 to 180° C.

3. The process as claimed in claim 1, wherein the gaseous reaction mixture comprising acrylic acid is cooled in stage A in a spray cooler.

4. The process as claimed in claim 1, further comprising stage B:

B: separating the gaseous mixture (2) comprising acrylic acid, to give a low-boiling fraction, a crude acrylic acid, and a bottom product, which bottom product comprises oligomeric acrylic acid.

5. The process as claimed in claim 4, wherein the separation of stage B is carried out in a distillation column and acrylic acid is obtained via a sidestream takeoff of the distillation column.

6. The process as claimed in claim 1, wherein some or all of the oligomeric acrylic acid is passed back into the cooling operation of stage A.

7. The process as claimed in claim 4, wherein the crude acrylic acid obtained in stage B is purified to obtain a product containing a higher concentration of acrylic acid than in said crude acrylic acid.

8. The process as claimed in claim 4, further comprising stage C:

C: esterifying the crude acrylic acid obtained in stage B with one or more alkanols.

9. The process as claimed in claim 4, wherein a portion of the quench bottom product obtained in stage A or of the bottom product obtained in stage B, or a mixture thereof, is heated in the presence of a catalyst, to give a mixture comprising acrylic acid.

10. The process as claimed in claim 8, wherein a portion of the quench bottom product obtained in stage A, which comprises oligomeric acrylic acid, and high-boiling byproducts obtained in the esterification of stage C are heated in whole or in part of the presence of a catalyst, to give a mixture comprising acrylic acid and acrylate.

11. The process as claimed in claim 9, wherein the mixture comprising acrylic acid is used for cooling in stage A.

12. The process as claimed in claim 7, wherein said crude acrylic acid obtained in stage B is purified by crystallization.

13. The process as claimed in claim 1, wherein neither gaseous reaction mixture (1) nor gaseous mixture (2) is subjected to an absorbent.

* * * * *